United States Patent [19]

Andou et al.

[11] Patent Number: 4,674,515
[45] Date of Patent: Jun. 23, 1987

[54] ULTRASONIC ENDOSCOPE

[75] Inventors: Outaro Andou, Hino; Eishi Ikuta, Hachiouji, both of Japan

[73] Assignee: Olympus Optical Co., Ltd., Tokyo, Japan

[21] Appl. No.: 790,573

[22] Filed: Oct. 23, 1985

[30] Foreign Application Priority Data

Oct. 26, 1984 [JP] Japan .............................. 59-162547[U]
Oct. 26, 1984 [JP] Japan .................................. 59-226478

[51] Int. Cl.⁴ ............................................ A61B 10/00
[52] U.S. Cl. .................................... 128/660; 128/661; 128/4; 128/6
[58] Field of Search ........................ 128/4, 6, 660, 661

[56] References Cited

U.S. PATENT DOCUMENTS 4,558,706 12/1985 Nakada et al. ........................... 128/4

FOREIGN PATENT DOCUMENTS 58-41539 3/1983 Japan .

Primary Examiner—Leo P. Picard
Attorney, Agent, or Firm—Armstrong, Nikaido, Marmelstein & Kubovcik

[57] ABSTRACT

Ultrasonic endoscope equipment transmits signals by providing a signal coupler such as rotary transformer or optical coupling device without using the signal line between the rotating part which introduces a signal line from an ultrasonic transducer housed in a rotatable way in the end of the inserting part of the endoscope and outputs the ultrasonic high frequency signal via a pre-amplifier and an ultrasonic image display unit which receives the ultrasonic high-frequency signal output from the rotating part and displays an ultrasonic image, the primary input side being provided on the output side of the said rotating part and the secondary output side on the input side of the said ultrasonic image display unit.

6 Claims, 8 Drawing Figures

ULTRASONIC ENDOSCOPE

FIELD OF THE INVENTION AND RELATED ART STATEMENT

This invention relates to an ultrasonic endoscope which can reproduce a clear image without containing noise in the received ultrasonic signals when rotating and scanning.

In the conventional ultrasonic endoscope, whose electrical configuration is shown in FIG. 1, an ultrasonic transducer 201 incorporated in the endoscope at its end is rotated by means of a flexible shaft and the signal is transmitted through the signal line 202, one end of which is connected to the said transducer 201 and another end to brush contacts 204 which is grounded and 203 which is connected to an external display unit 205 and a pulse generator 207 via a noise cutting diode 206.

Such a ultrasonic endoscope using brush contacts 203 and 204 has such advantage that noise is mixed in the received weak ultrasonic signal due to momentary separation of the brush contacts 203 and 204 during rotation or due to a change in the contact potential difference between the contacts forming the brush and the noise appears when a tomogram is displayed, thus making the tomogram difficult to be seen. Also there is an endoscope which has a motor housed at its end and the transducer connected to the rotating shaft of the motor, as disclosed in the Japanese Patent Journal No. 41539 in 1983, but it has the same disadvantage as the one shown in FIG. 1.

As an endoscope to reduce the aforementioned disadvantage, there is another conventional endoscope shown in FIG. 2.

This endoscope has a preamplifier 208 on the rotating side shown in a broken line to amplify the received ultrasonic signals of the transducer 201. Since this amplifier 208 also rotates in synchronism with that of the transducer 201, the brush contact 209 to supply power, brush contact 210 to output the output signal of the amplifier 208, brush contact 211 for common signal and brush contact 212 for applying the transmitting pulse are required. The noise cutting diode 206 is also provided on the rotating side. In such an endoscope, since the received ultrasonic signal is amplified before being passed through the brush contact 210, if the noise voltage occurring at the brush contact 210 is equivalent to that occurring at the brush contact 203 in FIG. 1, the S/N ratio will be improved in comparison with the configuration shown in FIG. 1. In this case, however, the DC current for power supply runs superposed on the signal current to the brush contact 211 provided in the common signal line, and this DC current poses a brush noise problem and causes the noise on the displayed picture image.

OBJECT AND SUMMARY OF THE INVENTION

The objective of this invention is to provide an ultrasonic endoscope which can display a clear picture image without brush noise on the received ultrasonic signal.

This invention has a signal coupling means, e.g. rotary transformer or optical coupling device, which transmits signals without using the signal line, between a rotating part which receives signals from an ultrasonic transducer housed rotary in the end of the inserting portion of an endoscope and outputs ultrasonic high-frequency signals via a preamplifier and an ultrasonic image display unit which receives the ultrasonic high-frequency signals output from the rotating part and displays the ultrasonic image, with its primary input side provided on the output side of the said rotating part and its secondary output side on the input side of the said ultrasonic image display unit.

DETAILED DESCRIPTION OF PREFERRED EMBODIMENTS

Figure 1:
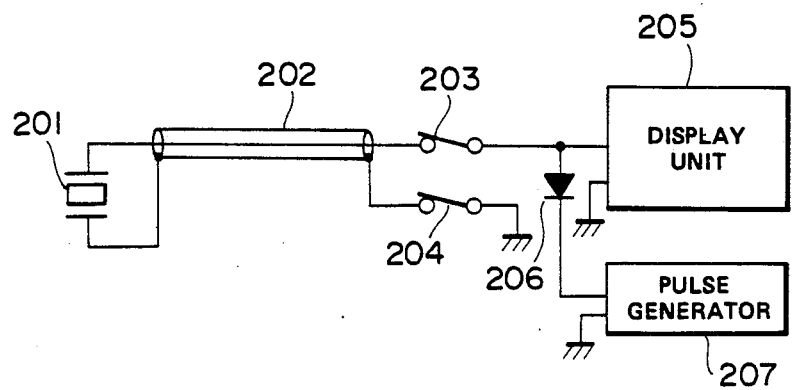
FIG. 1 is a circuit diagram showing components of the electrical system of a conventional ultrasonic endoscope.
Figure 2:
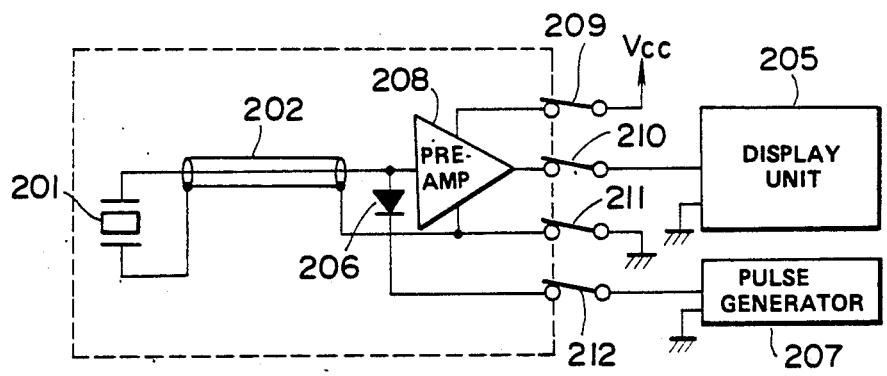
FIG. 2 is a circuit diagram showing components of the electrical system of another conventional ultrasonic endoscope.
Figure 3:
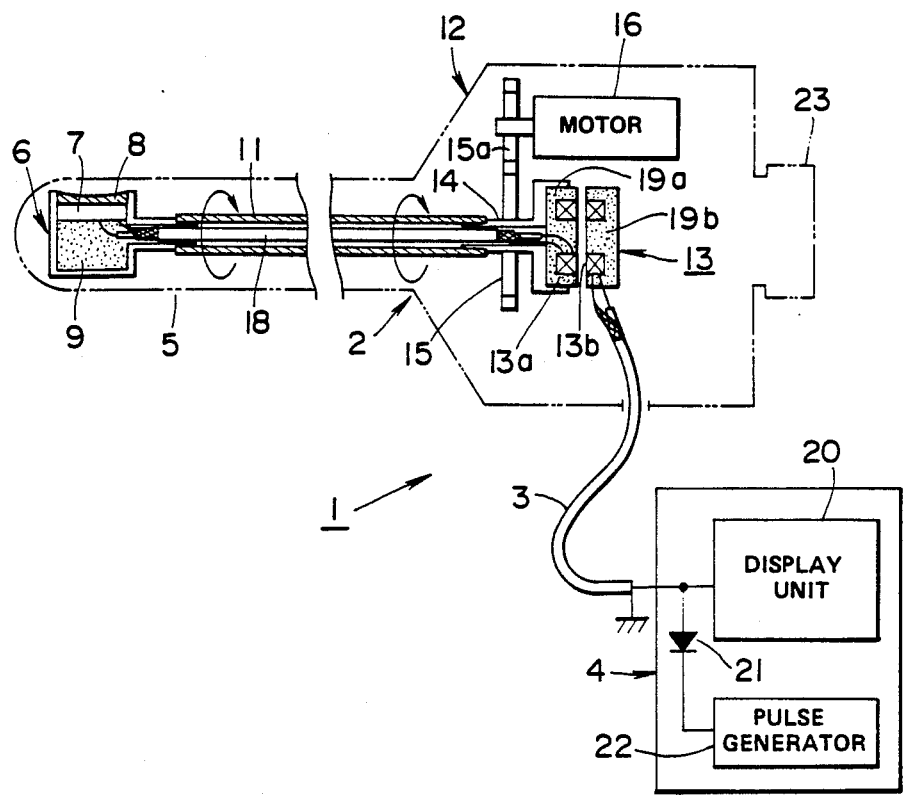
FIG. 3 is a schematic block diagram of the ultrasonic endoscope showing 1st embodiment of this invention.

FIG. 3 shows the 1st embodiment of this invention.

The ultrasonic endoscope equipment 1 in the 1st embodiment consists of an ultrasonic endoscope 2 provided with an observing means and ultrasonic wave receiving and transmitting means and a transmitting and receiving display unit 4 which is connected to the ultrasonic endoscope 2 via a coaxial cable 3.

The said ultrasonic endoscope 2 has an observing optical system and illuminating optical system (not illustrated) housed in the end of a narrow and hollow inserting part 5 which is inserted into a body cavity for observation and an ultrasonic transducer (ultrasonic probe) 6 at the end adjacent to the optical systems. The ultrasonic transducer part 6 consists of an ultrasonic transducer 7 which receives the ultrasonic wave caused by applying the high-frequency pulse for transmitting (transmitting pulse) and converts it into electrical signals, electrodes formed on its both sides, sound collecting acoustic lens 8 formed on one wave transmitting and receiving surface of the transducer 7, and damping member 9 provided on the other surface.

The said ultrasonic transducer part 6 is connected to the front end of a hollow flexible shaft 11 incorporated in the inserting part 5 and the rear end of the said flexible shaft 11 is brought into the operating section 12 and connected to the rotary shaft 14 of the rotary transformer 13. The rotary shaft 14 is provided with a gear 15 on its outer periphery, and the torque of the motor 16 is transmitted via a gear 15a which meshes with the said gear 15, and the ultrasonic transducer 6 is rotated via a rotation transmitting means of the flexible shaft 11.

The signal transmitting coaxial cable 18, one end of which is connected to both electrodes of the said ultrasonic transducer 6, is passed through the flexible shaft 11 and connected to the rotor coil 13a of the said rotary transformer 13 housed in the operating section 12.

The said rotary transformer 13 has mutually opposing magnetic cores 19a and 19b, and one core 19a is connected to the rotary shaft 14 and rotated in a state opposed to the other fixed core 19b.

On the mutually opposing surfaces of the said magnetic cores 19a and 19b, ring-like concave parts are formed, and in them the rotor coil 13a and stator coil 13b are housed, and AC signal applied to one coil is transmitted through electromagnetic induction to other opposing coil.

The said stator coil 13b is connected to the transmitting and receiving display unit 4 via the aforementioned coaxial cable 3.

The said transmitting and receiving display unit 4 consists of a display unit 20 to which the coaxial cable 3 is connected and a pulse generator 22 which is connected to the coaxial cable 3 via the diode 21.

The illuminating light source of the said ultrasonic endoscope 2 is housed in a light source unit (not illustrated and the light is sent through an illuminating light transmitting means and irradiated from its end surface toward a subject which can be image-formed by means of an observing optical system and the image of the subject can be observed from the rear of the eye-piece part 23 through the observing optical system.

According to the 1st embodiment thus constructed, since the transmission means for the transmitting pulse for irradiating the ultrasonic wave and for receiving signals is formed by using the rotary transformer 13 housed in the operating section 12 instead of the brush contact of the conventional example, the noise due to the brush contact can be eliminated and there is no possibility of the noise being mixed in the received signal, and so the ultrasonic tomogram with good S/N ratio can be displayed.

Also, since no sliding contact such as brush contact is used, a higher reliability and longer life can be achieved.

Figure 4:
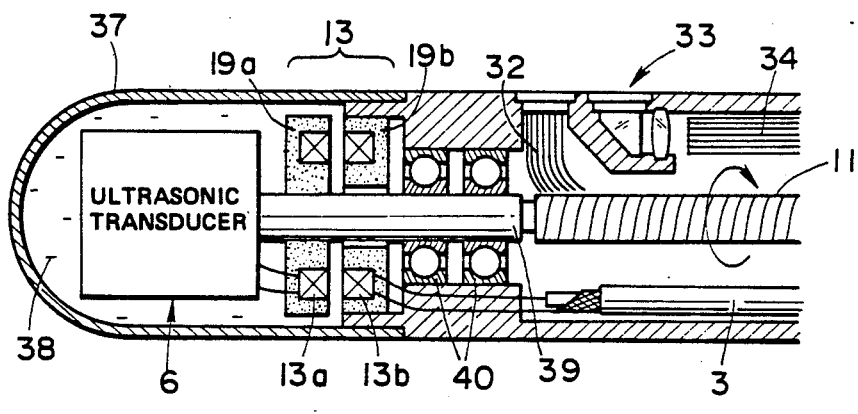
FIGS. 4 and 5 relate to 2nd embodiment of this embodiment and FIG. 4 is a cross section showing components of the 2nd embodiment and FIG. 5 a schematic block diagram showing the entirety of the 2nd embodiment.

FIG. 4 shows the 2nd embodiment of this invention.

In the 2nd embodiment, the rotary transformer 13 is housed in the end of the inserting part 5 instead of the operating section 12.

Figure 5:
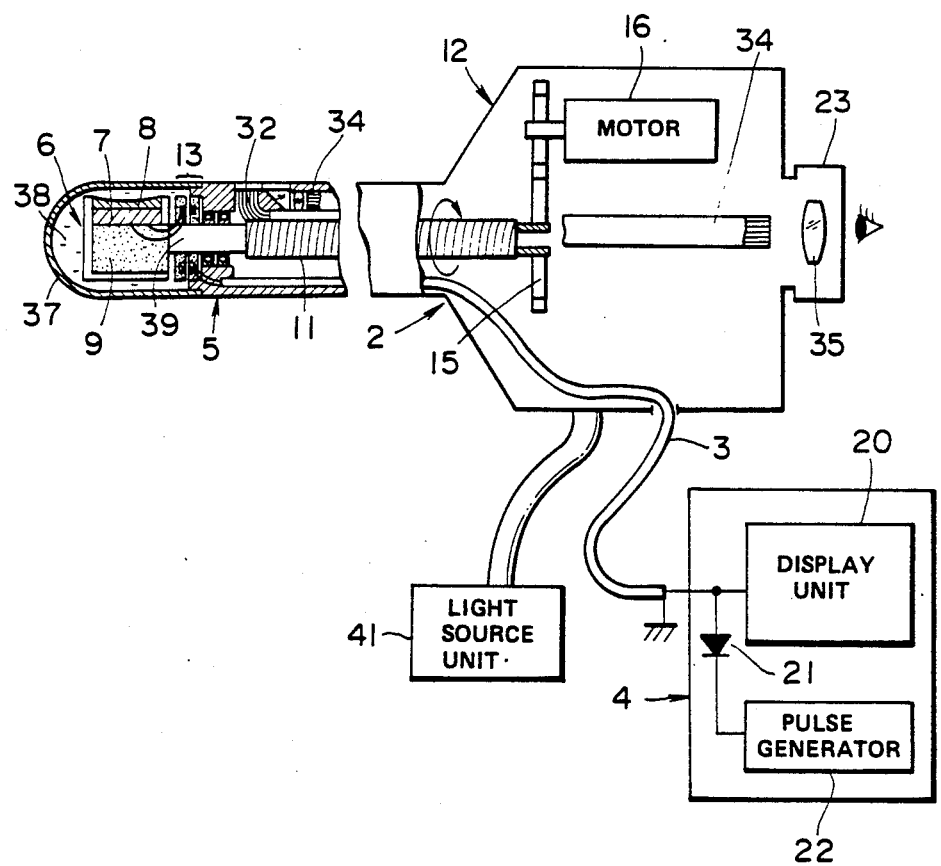

Inside the narrow and hollow inserting part 5, a light guide 32 is passed as an illuminating light transmitting means and irradiates the illuminating light from its end surface facing the side surface of the inserting part 5 at the end or near the end and illuminates a subject. Adjacent to the end surface of the light guide 32, an objective optical system 33 for observing is provided to form the image of the subject illuminated on the front end surface of the image guide 34 which acts as an image transmitting means and the image transmitted through the said image guide 34 to the other end surface (of the image guide 34) on the side of the operating section 12 shown in FIG. 5 can be observed from the rear of the eye-piece part 23 through the eye-piece.

The front end part of the inserting part 5 adjacent to the aforementioned observing means is covered with an ultrasonic wave transmitting resin cap 37 inside which an ultrasonic wave propagating medium 38 is filled. Inside the cap 37 which is filled with the ultrasonic wave propagating medium 38 an ultrasonic transducer 6 is housed and it is connected to a shaft 39 which is rotated. The shaft 39 is supported by bearings 40 which have sealing function, as shown in FIG. 4. Around the shaft 39 between the ultrasonic transducer 6 and bearings 40 a rotary transformer 13 is provided.

That is, the magnetic core 19a on the rotor side is installed on the shaft 39 and the opposing magnetic core 19b on the stator side is fixed to the inner wall of the inserting part 5. In the mutually opposing concentric concave parts in the magnetic cores 19a and 19b, rotor coil 13a and stator coil 13b are housed and fixed, and the rotor coil 13a is connected to the ultrasonic transducer 6 via the lead wire and the stator coil 13b to the coaxial cable 3 which is extended outside, in one-pieces (or via a connector).

The rear end of the said shaft 39 is connected to the front end of the flexible shaft 11 which is to be rotated by a motor 16 via a gear 15 in the operating section 12.

The light guide 32 as an illuminating light transmitting means is extended outside as a light guide cable from the operating section 12 and is to be fit to a light source unit 41.

According to the 2nd embodiment thus constructed, since the transmitting pulse signal and receiving signal transmitting means is formed by housing the rotary transformer 13 in the end of the inserting part 5 instead of using the brush contact of the conventional endoscope, the noise occurrence due to the brush contact and mixture of noise in the received signal can be avoided as in the case of the 1st embodiment.

Therefore, ultrasonic tomograms with good S/N ratio without brush noise can be obtained.

The said rotary transformer 13 can also be provided between the inserting part and the operating section, e.g. at the midway of the inserting part.

In the aforementioned embodiments the motor 16 is housed in the operating section 12, but it is also possible to house in the inserting part.

Figure 6:
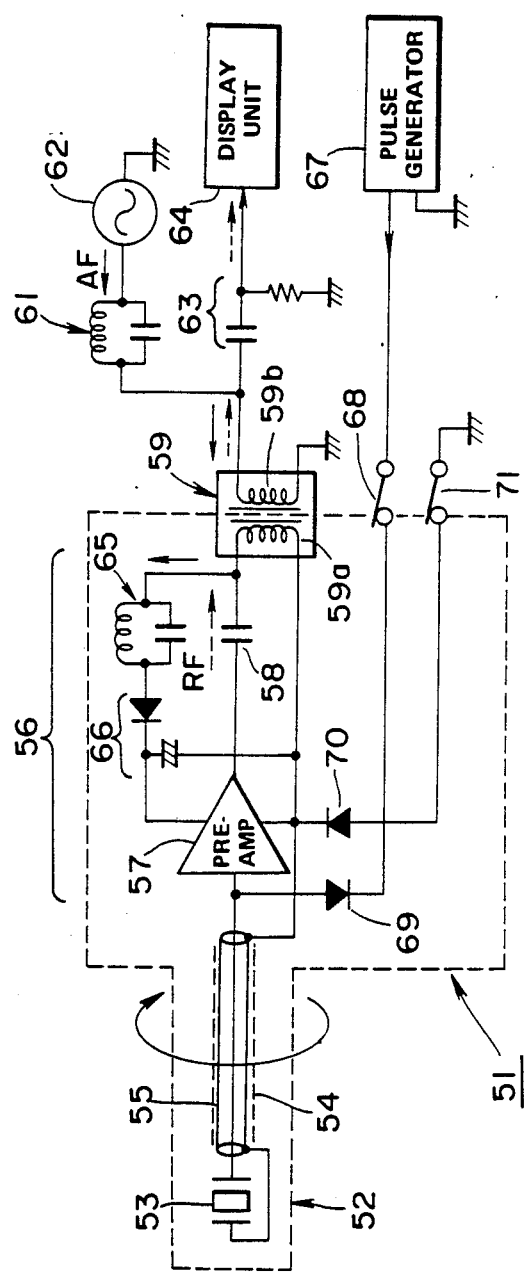
FIG. 6 is a circuit diagram showing components of the electrical system of 3rd embodiment of this invention.

FIG. 6 shows the 3rd embodiment of this invention.

The ultrasonic endoscope equipment 51 of the 3rd embodiment is provided with a ultrasonic transducer 53 to form the ultrasonic transducer part in the end part 52 of the endoscope, and the said ultrasonic transducer 53 is rotated by a driving means such as motor via a flexible shaft 54 (made of spiral tube, etc.—no specific shape is illustrated).

Through the flexible shaft 54 which is hollow, a coaxial cable 55 is passed, its one end connected to the transducer 53 and the other end introduced into the operating section. Inside the operating section an amplifier unit 56 is provided and is rotated together with the flexible shaft 54.

The other end of the cable connected to the said transducer 53 is connected to the input end of a preamplifier 57 with low noise figure in the amplifier unit 56. The output end of the preamplifier 57 is connected to one end of the rotor coil 59a of the rotary transformer 59 via a low-band cutting capacitor 58 or two-way high-pass filter (not illustrated). One end of the stator coil 59b of the rotary transformer 59 is connected to a sine-wave generator 62 which oscillates with a low frequency sufficiently lower than the operating frequency of the ultrasonic transducer 53, via a high-frequency trap 61 (formed, for example, by a coil and capacitor parallel resonance circuit), and the oscillating output is applied to the stator coil 59b of the rotary transformer 59 via the high-frequency trap 61. One end of the stator coil 59b is connected to the display unit 64 via a high-pass filter 63 formed, for example, a capacitor and resistance, and the high-frequency signals appearing on both sides of the stator coil 59b can be transmitted to the display unit 64. The other end of the stator coil 59b is grounded.

One end of the rotor coil 59a of the said rotary transformer 59 is connected to a rectifying/smoothing circuit 66 consisting of a diode and capacitor, via the 2nd high-frequency trap 65, and the smoothing output is connected to the power terminal of the preamplifier 57.

The output of the pulse generator 67 is connected to the cable 55 via the brush contact 68 and diode 69, and the common terminal of the amplifier unit 56 is connected to an external common signal line (return of the pulse generator 76) via the diode 70 and brush contact 71.

The portion surrounded by the broken line in FIG. 6 is rotated by a driving means such as motor.

The following will explain the operation of the 3rd embodiment thus constructed.

The high-frequency pulse generated by the pulse generator 67 passes through the brush 68 and diode 69 and is further transmitted through the cable 55 and applied to the transducer which is rotated, and the ultrasonic wave excited by the transducer 53 is sent toward a subject.

The ultrasonic wave reflected by the acoustic impedance discontinuous border surface of the subject excites the transducer 53 and the high-frequency electrical signal caused by the piezo-electric oscillation is passed through the cable 55 and amplified by the preamplifier 57. The amplified high-frequency signal (RF) is passed through the capacitor 58 and applied to the rotor coil 59a of the rotary transformer 59 as shown by the broken line arrow in the figure. In this case, the high-frequency signal is interrupted by the high-frequency trap 65 and does not go into the rectifying/smoothing circuit 66, and so the occurrence of damping, etc. is prevented. The high-frequency signal applied to the rotor coil 59a is transmitted to the stator coil 59b which is coupled with the said rotor coil 59a through induction and sent to the display unit 64 via the high-pass filter 63, and the ultrasonic tomogram is displayed on the display screen. The high-frequency signal transmitted to the said stator coil 59b is prevented by the high-frequency trap 61 from flowing into the low frequency sine-wave generator 62.

On the other hand, the low-frequency output (AF) of the generator 62 passes through the high-frequency trap 61, as shown by the solid line arrow in the figure, and is transmitted to the rotor coil 59a via the rotary transformer 59 (it is prevented by the high-pass filter 63 from going into the display unit 64), and it is further passed through the high-frequency trap 65 and smoothed into direct current by the rectifying/smoothing circuit 66 and then applied to the power terminal of the preamplifier 57 to maintain the preamplifier 57 in an operable condition. Although the low-frequency signal induced to the said rotor coil 59a passes through the rotary transformer 59 in the direction opposite to that of the high-frequency signal, its passage is interrupted by the capacitor (or high-pass filter) 58, and therefore, it does not affect the preamplifier 57.

Figure 7:
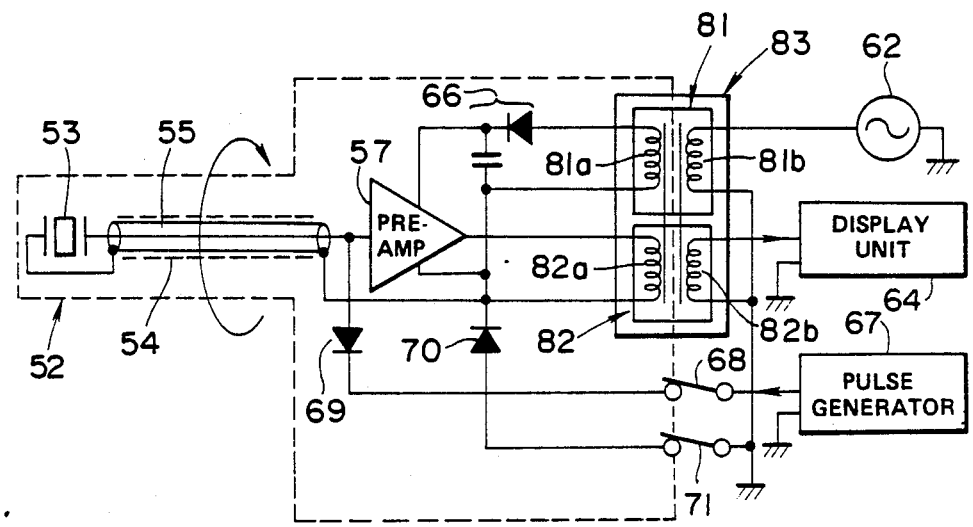
FIG. 7 is a circuit diagram showing components of the electrical system of 4th embodiment of this invention.

When the transmitting pulse is transmitted via the brush contact 68 or brush contact 71, the noise voltage occurring at the brush contacts 68 and 71 is normally lower than the forward voltage of the diode and therefore, is prevented by the diodes 69 or 70 and does not affect the receiving signal. FIG. 7 shows the 4th embodiment of this invention.

The 4th embodiment uses a rotary transformer 83 which is provided with 1st rotary transformer 81 and 2nd rotary transformer 82 and two places of the concentric circles with different radius. The stator coil 81b of the 1st rotary transformer 81 is connected to a low-frequency generator 62 and the rotor coil 81a is connected to the power terminal of the preamplifier 57 via the rectifying/smoothing circuit 66.

The stator coil 82b of the 2nd rotary transformer 82 is connected to the display unit 64 and the rotor coil 82a is connected to the output terminal of the preamplifier 27. The remaining is same as the 3rd embodiment. This 4th embodiment has a complicated structure of the rotary transformer 83, but the existing type which is now used for VTR, etc. can also be used. In this case, the frequency of the generator 62 is not restricted narrow as in the case of the 3rd embodiment. By inserting a short ring between the 1st and 2nd rotary transformers 81 and 82, sufficient insulation can be achieved.

It is also possible to construct in such a way that the transmitting pulse is transmitted through a rotary transformer without using the brush contact.

According to the aforementioned 3rd and 4th embodiments, the signal transmission is made by means of the rotary transformer without using the brush contact in the route of the receiving signal, the noise due to the brush contact is not mixed in the receiving signal and therefore, a tomogram with good S/N can be obtained. Also, since the receiving signal is amplified before being transmitted by the rotary transformer, the effect of the induced noise which tends to be mixed when the rotary transformer is used can be reduced. It is also possible to eliminate such trouble that may be caused by the brush noise of the power route of the amplifier.

Figure 8:
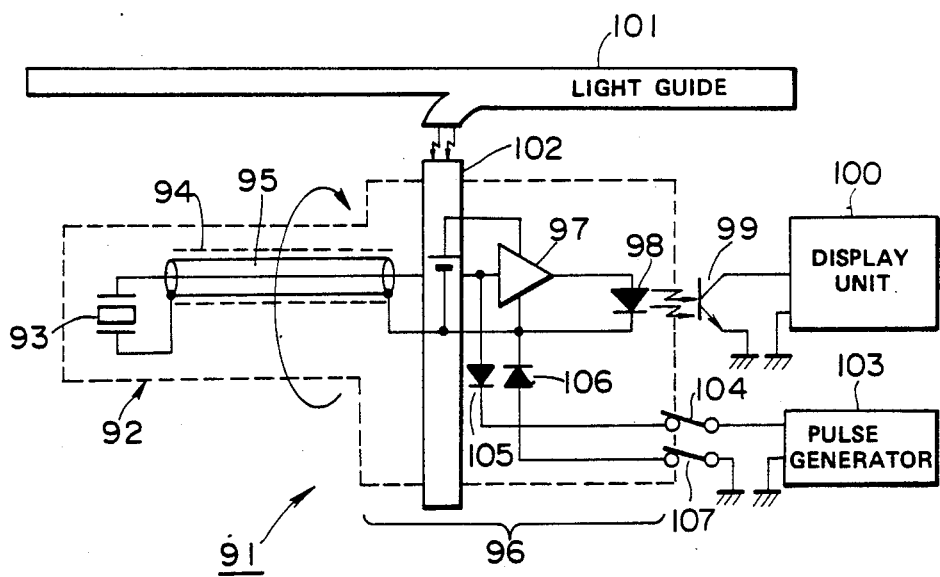
FIG. 8 is a circuit diagram showing components of the electrical system of 5th embodiment of this invention.

FIG. 8 shows the 5th embodiment of this invention.

The ultrasonic endoscope equipment 91 of the 5th embodiment is provided with an ultrasonic transducer 93 to form the ultrasonic transducer unit in the end part 92 of the endoscope and the ultrasonic transducer 93 is rotated by a driving means such as motor via a flexible shaft 94 (formed by spiral tube, etc.) passed through the inserting part.

In the hollow flexible shaft 94 a coaxial cable 95, one end of which is connected to the transducer 93, is passed and the other end of the cable 95 is introduced into the operating section. Inside the operating section an amplifier unit 96 is provided and it is rotated together with the flexible shaft 94.

The other end of the cable 95 connected to the said transducer 93 is connected to the input end of the preamplifier 97 with low noise figure in the amplifier unit 96. The output and of the preamplifier 97 is connected to one end of the light emission diode 98, the other end of which is connected to the common terminal of the amplifier unit 96 together with the common line for the amplifier 97, cable 95 and solar battery 102. The light emission diode 98 is provided together with the preamplifier 97 in the amplifier unit 96. As opposed to the light emission diode 98, a phototransistor 99 is fixed outside the amplifier unit 96 and the output end of the phototransistor is connected to the display unit 100 so that the high-frequency signals appearing on both ends of the photo-transistor can be transmitted to the display unit 100.

The power of the preamplifier existing in the rotating part shown in a broken line can be supplied to the power terminal of the preamplifier 97 by causing the electromotive force in the solar battery 102 provided ring-like around the rotating part by using part of the light of the illuminating optical system (light guide) 101.

The output of the pulse generator 103 is connected to the cable 95 via the brush contact 104 and diode 105, and the common terminal in the amplifier unit 96 is connected to the external common signal line (return of the pulse generator 103) via the diode 106 and brush contact 107.

In the 5th embodiment thus constructed, the high-frequency pulse generated by the pulse generator 103 is passed through the brush contact 104 and diode 105 and further through the cable 95 and applied to the transducer 93, and the ultrasonic wave excited by the transducer 93 is sent toward the subject. The ultrasonic wave reflected by the subject excites the transducer 93 and is converted into high-frequency electrical signal, passed through the cable 95 and then amplified by the preamplifier 97. The amplified high-frequency signal is converted into light signal by the light emission diode 98 and the light signal is received by the phototransistor 99 and after photoelectric conversion is made, it is sent to the display unit and the ultrasonic tomogram is displayed on the display screen. The power to operate the preamplifier 97 is obtained by irradiating part of the light from the light guide 101 to the solar battery 102. Since no brush contact is used in the receiving signal route and power supply route, there is no fear of the brush noise being mixed in the receiving signal, and since the rotating side and fixed side are coupled through optical coupling, there is no noise effect at the coupled point and the coupled part can be made smaller and lighter in weight. also, since the power supply in the endoscope and the external power supply are completely separated from each other, there is no noise through the power supply line and a tomogram with excellent S/N can be obtained. When the transmitting pulse is transmitted via the brush contact 104 or 107, the noise voltage occurring at the brush contact 104 or 107 is lower than the forward voltage of the diode, and therefore, it is prevented by the diode 105 or 106 and does not affect the receiving signal.

It is also possible to construct in such a way that the transmitting pulse is also transmitted via the rotary transformer without using the brush contact.

In the 5th embodiment, the high-frequency signal output from the preamplifier 97 is introduced into the display unit 100 through optical coupling, but it is also possible to replace the optical coupling with the capacity coupling where the rotating side and the fixed side form mutually opposed electrodes. In such a case, too, the power for the preamplifier 97 is obtained by means of the solar battery so that the power supply in the endoscope and the external power supply will be completely separated from each other.

We claim:

1. An ultrasonic endoscope, comprising:
    rotating means including an ultrasonic transducer disposed in an inserting end of an endoscope and a signal line connected with said transducer for outputting received high-frequency signals via a preamplifier;
    an ultrasonic image display means for receiving ultrasonic high-frequency signals output from said rotating means and displaying the resulting ultrasonic image; and
    a brushless signal coupling means for transmitting the ultrasonic high-frequency signals from said rotating means to said image display means, said coupling means including a primary input side provided on the output side of said rotating means and a secondary output side provided on the input side of the ultrasonic image display means.

2. The ultrasonic endoscope of claim 1, further comprising:
    a generator connected to the stator coil of said rotary transformer for outputting an AC signal with sufficiently lower frequency than the operating frequency of said ultrasonic transducer;
    a rectifying/smoothing circuit connected to the rotor coil of said rotary transformer for rectifying said AC signal; and
    wherein the rectified/smoothed output from said rectifying/smoothing circuit is used as a power supply for said preamplifier.

3. The ultrasonic endoscope of claim 1, wherein said brushless signal coupling means is a rotary transformer, its primary input side being a rotor coil and its secondary output side being a stator coil.

4. The ultrasonic endoscope of claim 1, wherein said brushless signal coupling means is an optical coupling means, having its primary input side being a light emitted element and its secondary output side being a light receiving element.

5. The ultrasonic endoscope of claim 1, wherein said brushless signal coupling means is a capacity coupling means whose primary input side and secondary output side form mutually opposing electrodes.

6. The ultrasonic endoscope of one of claims 1, 4, or 5, wherein power supplied to said preamplifier is generated by a solar battery disposed around said rotating part, said solar battery receiving light from the illuminating optical system.

* * * * *